United States Patent

Henshall et al.

[11] Patent Number: 5,908,961
[45] Date of Patent: Jun. 1, 1999

[54] PRODUCTION OF AMINOPHENOLS

[75] Inventors: John Barry Henshall, Urmston; John Whitworth, Audenshaw; Ian Antony Dearden, Crumpsall; Steven Walsh, Warrington, all of United Kingdom

[73] Assignee: Ciba Specialty Chemicals Corporation, Tarrytown, N.Y.

[21] Appl. No.: 08/932,328

[22] Filed: Sep. 17, 1997

[30] Foreign Application Priority Data

Sep. 19, 1996 [GB] United Kingdom ............... 9619532
Mar. 1, 1997 [GB] United Kingdom ............... 9704287

[51] Int. Cl.$^6$ ............................................. C07C 209/38
[52] U.S. Cl. ................................................... 564/404
[58] Field of Search ........................................ 564/404

[56] References Cited

U.S. PATENT DOCUMENTS 2,286,475  6/1942  Egloff et al. ..................... 44/9
2,541,655  2/1951  Levis, Jr. ........................ 260/577

FOREIGN PATENT DOCUMENTS 0218350  4/1987  European Pat. Off. .
1241105  7/1971  United Kingdom .

OTHER PUBLICATIONS

Grimme, Schmitz: "Über die Dartsellung von N,N–(Bis–n–-butyl–m–amino phenol" Chemische Berichte., vol. 84, 1951, p. 740.

*Primary Examiner*—Brian M. Burn
*Attorney, Agent, or Firm*—Kevin T. Mansfield

[57] ABSTRACT

A method of producing N,N-disubstituted aminophenols of the general formula

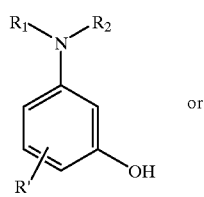

(I)

or

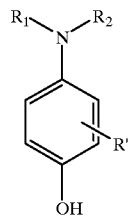

(II)

wherein $R_1$ and $R_2$ are the same or different and each represents a saturated or unsaturated aliphatic hydrocarbyl, cycloalkyl, aralkyl, the phenyl ring of which may be further substituted, alkoxyalkyl, or a cycloalkylalkyl, except that $R_1$ and $R_2$ are not simultaneously methyl and R' represents hydrogen, halogen, nitro, cyano, alkyl or alkoxy, which comprises reacting an aminophenol of general formula

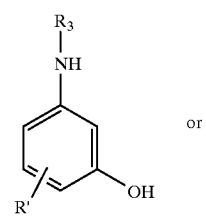

(III)

or

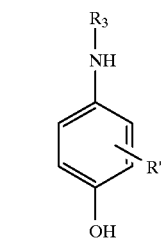

(IV)

wherein $R_3$ represents hydrogen or $R_1$, and R' is as defined above, with an organic halide species of general formula $R_2X$ wherein $R_2$ is as defined above and X is halogen under aqueous acidic conditions with the periodic addition of an acid trapping agent in such a way that continuous monitoring of pH is not required.

16 Claims, No Drawings

PRODUCTION OF AMINOPHENOLS

PRODUCTION OF AMINOPHENOLS

This invention relates to a method of producing N,N-disubstituted aminophenols. N,N-Disubstituted aminophenols are useful intermediates for the preparation of fluoran compounds used as dyestuffs in pressure- or heat-sensitive recording systems.

3-N,N-dialkylaminophenols have been produced by the alkylation of 3-aminophenol with alkyl halides under a number of reaction conditions, for instance

- a] butylation of 3-aminophenol with butyl iodide in the presence of $C_1$–$C_4$ alcohol and an alkali metal carbonate as an acid trapping agent under reflux conditions as disclosed in JP 02101053, Chemical Abstract volume 113, 40149.
- b] butylation of 3-aminophenol in an aqueous system under reflux for 24 hours in the presence of potassium hydroxide as an acid trapping agent as disclosed in Chem. Ber. 1951 (84) 740.
- c] alkylation of 3-aminophenol using an alkyl bromide in ethanol at reflux followed by isolation of 3-N-alkylaminophenol. This 3-N-alkylaminophenol can then be treated in a like manner to give the desired 3-N,N-dialkylaminophenol as disclosed in JACS 1952 (74) 573–578. The same workers describe a modification in which, after the formation of the 3-N-alkylaminophenol in ethanol the reaction mass is diluted with an aqueous solution of sodium carbonate and the alkylation completed by the addition of further alkyl bromide.
- d] alkylation of 3-aminophenol with an alkyl halide in dimethyl-formamide as solvent at room temperature in the presence of a base such as triethylamine as disclosed in USSR 523080, Chemical Abstract volume 85, 177057.
- e] alkylation of 3-aminophenol with a 1-iodoalkane in the presence of N,N-diisopropylethylamine in refluxing methanol as disclosed in EP 356173.
- f] autoclaving 3-aminophenol with an alkyl halide in the presence of water and ammonia at 100° C. as disclosed in JP 62048653, Chemical Abstract volume 107, 58645. The same workers describe an improvement in yield by controlling the pH to $\geq 4.0$ by continuously feeding ammonia to the autoclave during the alkylation.

The above methods, as described in a] to f] are disadvantageous for industrial manufacture in some part of their processing, namely

- a] the use of an organic solvent and a relatively expensive alkyl halide in the form of an alkyl iodide.
- b] no pH control during the alkylation leading to poor yields of the desired product and the need to carry out a purification step in order to remove undesirable by-products such as O-alkylated moieties.
- c] the use of an organic solvent during the alkylation steps.
- d] the use of an organic solvent and a relatively expensive organic base as the acid trapping agent.
- e] the use of an organic solvent together with a relatively expensive alkyl halide, in the form of an alkyl iodide, and an organic base.
- f] carrying out the reaction at elevated pressure requiring the need for an autoclave together with the use of ammonia and the technical difficulties associated with continuously monitoring pH in such a reaction environment.

4-N,N-Dialkylaminophenols have been made in a like manner to the 3-N,N-dialkylaminophenols as just described, namely in the presence of organic solvents or by the use of less convenient or more expensive reagents.

It is, therefore, an object of the invention to provide a method of producing N,N-disubstituted aminophenols of high purity and high yield by the reaction of an organic halide species, defined later with an aminophenol or N-substituted aminophenol, under aqueous acidic conditions with the periodic addition of an acid trapping agent in such a way that continuous monitoring of pH is not required.

The invention provides a method of producing N,N-disubstituted aminophenols having the general formula

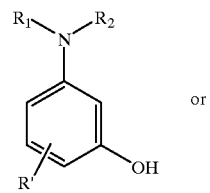

(I)

or

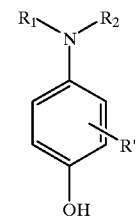

(II)

wherein $R_1$ and $R_2$ are the same or different and each represents a saturated or unsaturated aliphatic hydrocarboyl, cycloalkyl, aralkyl, the phenyl ring of which may be further substituted, alkoxyalkyl, or a cycloalkylalkyl, except that $R_1$ and $R_2$ are not simultaneously methyl and R' represents hydrogen, halogen, nitro, cyano, alkyl or alkoxy, which comprises reacting, in an aqueous system, a compound of formula

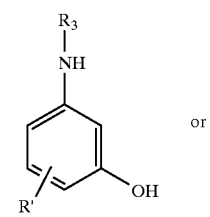

(III)

or

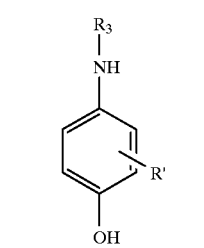

(IV)

wherein $R_3$ represents hydrogen or $R_1$, and R' represents hydrogen, halogen, nitro, cyano, alkyl containing 1 to 2 carbon atoms or alkoxy containing 1 to 2 carbon atoms with an organic halide species of general formula $R_2X$ wherein $R_2$ is as defined above and X is halogen, under aqueous acidic conditions with the periodic and controlled addition of acid trapping agent but without the need for continuously monitoring the pH of the reaction mass. As halogen X may be chlorine, bromine or iodine, but is preferably bromine as in some cases the organic chlorides are not sufficiently reactive. The reaction is preferably carried out at 0–2 bar pressure thus obviating the need for specialised equipment such as an autoclave although higher pressures may be employed if so desired. The benefit of using inorganic acid trapping agents is the fact that the resultant halogen salt is soluble in the aqueous medium, is readily removed from the reaction mass by simple phase separation and requires minimal treatment prior to discharge to the effluent system. Organic acid trapping agents may also be used but in this instance additional steps are required to recover the organic base prior to discharge to the effluent system.

Aminophenols which may be used in the invention include 3-aminophenol, 4-aminophenol, 4-amino-3-methylphenol, 4-amino-3-chlorophenol, 4-amino-3-nitrophenol, 3-N-methylaminophenol, 3-N-ethylaminophenol, 3-N-n-propylaminophenol, 3-N-isopropylaminophenol, 3-N-n-butylaminophenol, 3-N-isobutylaminophenol, 3-N-secbutylaminophenol, 3-N-n-pentylaminophenol, 3-(N-1'-methylbutylamino)phenol, 3-N-isoamylaminophenol, 3-(N-1'-methylpentylamino)phenol, 3-(N-cyclohexylamino)phenol, 3-N-hexylaminophenol, 3-N-ethoxypropylaminophenol, 3-N-cyclohexylmethylaminophenol, 3-N-phenethylaminophenol, 4-N-methylaminophenol, 4-N-ethylaminophenol, 4-N-n-propylaminophenol, 4-N-isopropylaminophenol, 4-N-n-butylaminophenol, 4-N-isobutylaminophenol, 4-N-secbutylaminophenol, 4-N-n-pentylaminophenol, 4-(N-1'-methylbutylamino)phenol, 4-N-isoamylaminophenol, 4-(N-1'-methylpentylamino)phenol, 4-(N-cyclohexylamino)phenol, 4-N-hexylaminophenol, 4-N-ethoxypropylaminophenol, 4-N-cyclohexylmethylaminophenol, and 4-N-phenethylaminophenol.

The aminophenol derivative of formula III or IV is reacted with an organic halide species of general formula $R_2X$ wherein $R_2$ and X are as described above in an aqueous medium.

As saturated aliphatic hydrocarbyl groups, there may be mentioned especially linear or branched alkyl groups containing 1 to 18 carbon atoms. As unsaturated aliphatic hydrocarbyl groups there may be mentioned linear or branched alkenyl groups having 3 to 5 carbon atoms and alkynyl groups having 3 carbon atoms. As cycloalkyl groups, there may be mentioned especially cycloalkyl groups of 5 to 7 carbon atoms in which the cycloalkyl ring may be further substituted by methyl. As aralkyl groups, there may be mentioned especially aralkyl groups containing 7 to 8 carbon atoms. In addition the aromatic ring of the aralkyl group may be further substituted. As alkoxyalkyl groups, there may be mentioned especially alkoxyalkyl groups of 2 to 4 carbon atoms. As cycloalkylalkyl groups, there may be mentioned especially cycloalkylalkyl groups of 6 to 8 carbon atoms. In addition there may be further substitution by, for example, an alkyl group such as methyl.

Organic halides which may be used in the invention include methyl chloride, methyl bromide, methyl iodide, ethyl chloride, ethyl bromide, propyl bromide, n-butyl bromide, isoamyl bromide, n-hexyl bromide, cyclohexylmethyl bromide, allyl bromide, crotyl bromide, 4-bromo-2-methyl-2-butene and propargyl bromide.

The organic halide species is usually used in an amount of 2.0 to 2.5, more preferably 2.0 to 2.15 moles per mole of the aminophenol derivative of formula III or IV when $R_3$ is hydrogen. When $R_3$ is other than hydrogen, the organic halide species is usually used in an amount of 1.0 to 1.25, more preferably 1.0 to 1.15 moles per mole of the N-substituted aminophenol derivative. The reaction is effected in the presence of water, the total amount used being sufficient to dissolve all the inorganic salts prior to isolation of the N,N-disubstituted aminophenol by phase separation and washing, if desired.

The reaction is preferably carried out in a stepwise manner. Thus approximately half the required organic halide species is added to an aqueous slurry or solution of the aminophenol derivative. The temperature of the reaction may be between room temperature and the boiling point of the reaction mass, more specifically between 50° C. and the boiling point of the reaction mass and the reaction time may vary from 1 hour to many hours depending upon the temperature of the reaction and the chosen reactants. After this initial reaction an acid trapping agent is added in an amount sufficient to neutralise most of the acid generated, present largely as the hydrohalide salt of the aminophenol derivative. An exact pH is not required and the aminophenol derivative is released for subsequent reaction, but the pH is not allowed to exceed 7.0. A further quantity of the organic halide species is added and the reaction continued with conditions as described in the first step of the procedure. A further quantity of the acid trapping agent is then added to adjust the pH as before. The final portion of the organic halide species is then added and the reaction continued to completion.

The number of steps chosen for the reaction need not be limited to 3 as described above but should preferably be greater than 1. Reaction of the phenol moiety of the aminophenol derivative is inhibited by ensuring that the pH of the reaction mass does not exceed pH 7. If the pH exceeds this value then there is a greater chance of producing unwanted impurities that may be detrimental to the subsequent use of the final isolated product.

As acid trapping agents there may be mentioned, but not limited by, the following examples:

metal hydroxides from Groups 1 and 2 of the Periodic Table such as lithium hydroxide, sodium hydroxide, potassium hydroxide, magnesium hydroxide and calcium hydroxide which may be used as a solid, aqueous solution or aqueous slurry;

metal carbonates from Groups 1 and 2 of the Periodic Table such as lithium carbonate, sodium carbonate, potassium carbonate, calcium carbonate and magnesium carbonate which may be used as a solid, aqueous solution or aqueous slurry;

metal bicarbonates from Group 1 of the Periodic Table such as sodium bicarbonate and potassium bicarbonate to which may be used as a solid, aqueous solution or aqueous slurry.

As acid trapping agents there may also be used magnesium oxide. Isolation may be by phase separation of the desired N,N-disubstituted aminophenol from an aqueous solution of inorganic salts. The organic phase may be washed with water containing sufficient acid trapping agent as to ensure that the pH is sufficiently high to neutralise any remaining hydrohalide salts of the product whilst ensuring that the pH is not too high as to initiate reaction of the phenol moiety with traces of the organic halide species that may be remaining.

If desired a solvent immiscible with water may be added prior to the isolation in order to improve the efficiency of the phase separation. Examples of solvents which may be used include aromatic hydrocarbons such as benzene, toluene and xylene; chlorinated aromatic hydrocarbons such as chlorobenzene and dichlorobenzenes; straight chain or branched chain aliphatic hydrocarbons which may be saturated or unsaturated and which may be further substituted by chlorine, for example perchlorethylene; cycloalkyl compounds of 5 to 7 carbon atoms such as cyclohexane.

Additionally, if it is desired to minimise the aqueous effluent produced from the process then the total water usage may be reduced to a level wherein the inorganic salts are not totally dissolved. In this instance a filtration step can be introduced to remove and recover these inorganic salts.

The organic layer, after phase separation may then be dried by distillation either under atmospheric conditions or under vacuum conditions. It is also preferred that the distillation and storage should be carried out in an inert atmosphere such that oxidation products cannot be formed.

The invention will now be described in more detail with reference to examples but the invention should not be considered as being limited to the examples herein.

EXAMPLE 1

3-N,N-Dibutylaminophenol

Water (200 g) and 3-aminophenol (218 g; 2.00 mole) are charged to a reactor and heated to 80° C. n-Butyl bromide (328.8 g; 2.40 mole) is then added whilst maintaining the vessel contents at a temperature of 80–85° C. The reaction mass is stirred for a further 1 hour at 80–85° C.

Sodium hydroxide solution 47% (140 g; 1.64 mole) is then added. The temperature is adjusted to 90–93° C. and then n-butyl bromide (192 g; 1.40 mole) is added whilst maintaining the temperature at 90–93° C. The reaction mass is stirred for a further 1 hour within this temperature range then sodium hydroxide solution 47% (93 g; 1.09 mole) is added. A final portion of n-butyl bromide (68.4 g; 0.5 mole) is added and the reaction mass then stirred for 13 hours at a temperature of 91–95° C.

The vessel contents are cooled to 70–75° C. and water (120 g) is added. The temperature is adjusted to 70–75° C. and then sodium hydroxide solution 47% (88.5 g; 1.04 mole) is added to obtain a pH within the range 4.4 and 5.0. The vessel contents are allowed to settle into 2 layers and the lower aqueous layer then removed.

To the oily organic layer is added water (400 g) and sodium carbonate 100% (24 g; 0.23 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (400 g) and sodium carbonate 100% (1.0 g) is added and the washing procedure repeated with the pH of the aqueous phase between 6.0 and 7.0. Following separation of the aqueous layer the oily organic layer is dried under vacuum. The yield of 3-N,N-dibutylaminophenol is 95.3% theory.

EXAMPLE 2

3-N,N-Dibutylaminophenol

Example 1 is repeated with sodium hydroxide solution 47% additions being replaced by the equivalent quantities of sodium carbonate 100%.

The yield of 3-N,N-dibutylaminophenol is 94.7% theory.

EXAMPLE 3

3-N,N-Dihexylaminophenol

Water (100 g) and 3-aminophenol (109 g; 1.00 mole) are charged to a reactor and heated to 80° C. n-Hexyl bromide (198.1 g; 1.20 mole) is then added whilst maintaining the vessel contents at a temperature of 80–85° C. The reaction mass is stirred for a further 1 hour at 80–85° C.

Sodium hydroxide solution 47% (70 g; 0.82 mole) is then added. The temperature is adjusted to 90–93° C. and then n-hexyl bromide (115.7 g; 0.7 mole) is added whilst maintaining the temperature at 90–93° C. The reaction mass is stirred for a further 1 hour within this temperature range then sodium hydroxide solution 47% (46.5 g; 0.545 mole) is added. A final portion of n-hexyl bromide (41.2 g; 0.25 mole) is added and the reaction mass then stirred for 13 hours at a temperature of 91–95° C.

The vessel contents are cooled to 70–75° C. and water (60 g) is added. The temperature is adjusted to 70–75° C. and then sodium hydroxide solution 47% (44.25 g; 0.52 mole) is added. The vessel contents are allowed to settle into 2 layers and the lower aqueous layer then removed.

To the oily organic layer is added water (200 g) and sodium carbonate 100% (12 g; 0.115 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (200 g) and sodium carbonate 100% (1.0 g) is added and the washing procedure repeated with the pH of the aqueous phase between 6.0 and 7.0. Following separation of the aqueous layer the oily organic layer is dried under vacuum. The yield of 3-N,N-dihexylaminophenol is 89.4% theory.

EXAMPLE 4

3-N,N-Diisoamylaminophenol

Water (100 g) and 3-aminophenol (109 g; 1.00 mole) are charged to a reactor and heated to 80° C. Isoamyl bromide (181.2 g; 1.20 mole) is then added whilst maintaining the vessel contents at a temperature of 80–85° C. The reaction mass is stirred for a further 1 hour at 80–85° C.

Sodium hydroxide solution 47% (70 g; 0.82 mole) is then added. The temperature is adjusted to 90–93° C. and then isoamyl bromide (105.7 g; 0.7 mole) is added whilst maintaining the temperature at 90–93° C. The reaction mass is stirred for a further 1 hour within this temperature range then sodium hydroxide solution 47% (46.5 g; 0.545 mole) is added. A final portion of isoamyl bromide (37.7 g; 0.25 mole) is added and the reaction mass then stirred for 13 hours at a temperature of 91–95° C.

The vessel contents are cooled to 70–75° C. and water (60 g) is added. The temperature is adjusted to 70–75° C. and then sodium hydroxide solution 47% (44.25 g; 0.52 mole) is added. The vessel contents are allowed to settle into 2 layers and the lower aqueous layer then removed.

To the oily organic layer is added water (200 g) and sodium carbonate 100% (12 g; 0.115 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (200 g) and sodium carbonate 100% (1.0 g) is added and the washing procedure repeated with the pH of the aqueous phase between 6.0 and 7.0. Following separation of the aqueous layer the oily organic layer is dried under vacuum. The yield of 3-N,N-diisoamylaminophenol is 91.4% theory.

EXAMPLE 5

3-N,N-Dicyclohexylmethylaminophenol

Water (15 g) and 3-aminophenol (16.4 g; 0.15 mole) are charged to a reactor and heated to 80° C. Cyclohexylmethyl bromide (31.9 g; 0.18 mole) is then added whilst maintaining the vessel contents at a temperature of 80–85° C. The reaction mass is stirred for a further 16 hour at 80–85° C.

Sodium hydroxide solution 47% (10.4 g; 0.12 mole) is then added. The temperature is adjusted to 90–93° C. and then cyclohexymethyl bromide (18.6 g; 0.105 mole) is added whilst maintaining the temperature at 90–93° C. The reaction mass is stirred for a further 4.5 hour within this temperature range then sodium hydroxide solution 47% (7.0 g; 0.08 mole) is added. A final portion of cyclohexylmethyl bromide (6.6 g; 0.037 mole) is added and the reaction mass then stirred for 16 hours at a temperature of 91–95° C.

The vessel contents are cooled to 70–75° C. and water (9 g) is added. The temperature is adjusted to 70–75° C. and then sodium hydroxide solution 47% (6.6 g; 0.08 mole) is added. Toluene (150 g) is added and the vessel contents are allowed to settle into 2 layers and the lower aqueous layer then removed.

To the toluene solution is added water (150 g) and sodium carbonate 100% (1.8 g; 0.017 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. The toluene is then removed by distillation.

The yield of 3-N,N-dicyclohexylmethylaminophenol is 83.8% theory.

EXAMPLE 6

4-N,N-Dibutylaminophenol

Water (150 g) and 4-aminophenol (109 g; 1.00 mole) are charged to a reactor and heated to 80° C. n-Butyl bromide (164.4 g; 1.20 mole) is then added whilst maintaining the vessel contents at a temperature of 80–85° C. The reaction mass is stirred for a further 1 hour at 80–85° C.

Sodium hydroxide solution 47% (70 g; 0.82 mole) is then added. The temperature is adjusted to 90–93° C. and then n-butyl bromide (96 g; 0.7 mole) is added whilst maintaining the temperature at 90–93° C. The reaction mass is stirred for a further 1 hour within this temperature range then sodium hydroxide solution 47% (46.5 g; 0.54 mole) is added. A final portion of n-butyl bromide (34.2 g; 0.25 mole) is added and the reaction mass then stirred for 13 hours at a temperature of 91–95° C.

The vessel contents are cooled to 70–75° C. and water (60 g) is added. The temperature is adjusted to 70–75° C. and then sodium hydroxide solution 47% (44.3 g; 0.52 mole) is added to obtain a pH within the range 4.4 and 5.0. The vessel contents are allowed to settle into 2 layers and the lower aqueous layer then removed.

To the oily organic layer is added water (200 g) and sodium carbonate 100% (12 g; 0.115 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (200 g) and sodium carbonate 100% (1.0 g) is added and the washing procedure repeated with the pH of the aqueous phase between 6.0 and 7.0. Following separation of the aqueous layer the oily organic layer is dried under vacuum. The yield of 4-N,N-dibutylaminophenol is 91.9% theory.

EXAMPLE 7

3-N,N-Dibutylaminophenol

Water (200 g) and 3-N-n-butylaminophenol (330 g; 2.00 mole) are charged to a reactor and heated to 80° C. n-Butyl bromide (164.4 g; 1.20 mole) is then added whilst maintaining the vessel contents at a temperature of 90–93° C. The reaction mass is stirred for a further 1 hour at 90–93° C.

Sodium hydroxide solution 47% (70 g; 0.82 mole) is then added. The temperature is readjusted to 90–93° C. and then n-butyl bromide (130.2 g; 0.95 mole) is added whilst maintaining the temperature at 90–93° C. The reaction mass is stirred for 13 hours at a temperature of 91–95° C.

The vessel contents are cooled to 70–75° C. and water (60 g) is added. The temperature is adjusted to 70–75° C. and then sodium hydroxide solution 47% (90.8 g; 1.06 mole) is added to obtain a pH within the range 4.4 and 5.0. The vessel contents are allowed to settle into 2 layers and the lower aqueous layer then removed.

To the oily organic layer is added water (400 g) and sodium carbonate 100% (12 g; 0.115 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (400 g) and sodium carbonate 100% (1.0 g) is added and the washing procedure repeated with the pH of the aqueous phase between 6.0 and 7.0. Following separation of the aqueous layer the oily organic layer is dried under vacuum.

EXAMPLE 8

3-N-Butyl-N-isoamylaminophenol

This is prepared by repeating Example 7 with 3-N-butylaminophenol being replaced by 3-N-isoamylaminophenol.

EXAMPLE 9

3-N-Ethyl-N-isoamylaminophenol

This is prepared by repeating Example 7 with 3-N-butylaminophenol being replaced by 3-N-ethylaminophenol and butyl bromide being replaced by isoamyl bromide.

EXAMPLE 10

4-N,N-Dibutylaminophenol

Water (150 g) and 4-N-n-butylaminophenol (330 g; 2.00 mole) are charged to a reactor and heated to 80° C. n-Butyl bromide (164.4 g; 1.20 mole) is then added whilst maintaining the vessel contents at a temperature of 90–93° C. The reaction mass is stirred for a further 1 hour at 90–93° C.

Sodium hydroxide solution 47% (70 g; 0.82 mole) is then added. The temperature is adjusted to 90–93° C. and then n-butyl bromide (96 g; 0.7 mole) is added whilst maintaining the temperature at 90–93° C. The reaction mass is stirred for a further 1 hour within this temperature range then sodium hydroxide solution 47% (46.5 g; 0.54 mole) is added. A final portion of n-butyl bromide (34.2 g; 0.25 mole) is added and the reaction mass then stirred for 13 hours at a temperature of 91–95° C.

The vessel contents are cooled to 70–75° C. and water (60 g) was added. The temperature is adjusted to 70–75° C. and then sodium hydroxide solution 47% (44.3 g; 0.52 mole) is added to obtain a pH within the range 4.4 and 5.0. The vessel contents are allowed to settle into 2 layers and the lower aqueous layer then removed.

To the oily organic layer is added water (200 g) and sodium carbonate 100% (12 g; 0.115 mole). The reaction mass temperature is adjusted to 70–75° C. and the vessel contents agitated to allow thorough mixing and with the pH of the aqueous layer between 6.0 and 7.0. The vessel contents are allowed to settle and the lower aqueous layer removed. A further quantity of water (200 g) and sodium carbonate 100% (1.0 g) is added and the washing procedure repeated with the pH of the aqueous phase between 6.0 and 7.0. Following separation of the aqueous layer the oily organic layer is dried under vacuum.

EXAMPLE 11

3-N-Butyl-N-isopropylaminophenol

This is prepared by repeating Example 7 with 3-N-butylaminophenol being replaced by 3-N-isopropylaminophenol.

EXAMPLE 12

3-N-Butyl-N-ethylaminophenol

This is prepared by repeating Example 7 with 3-N-butylaminophenol being replaced by 3-N-ethylaminophenol.

EXAMPLE 13

3-N,N-Diallylaminophenol

Water (20 g) and 3-aminophenol (21.8 g; 0.2 mole) are charged to a reactor and heated to 75° C. Allyl bromide (29.1 g; 0.24 mole) is then added whilst maintaining the vessel contents at a temperature of 75° C. The reaction mass is stirred for a further 3 hours at 75° C. Sodium carbonate (8.7 g; 0.082 mole) is then added. Allyl bromide (22.95 g; 0.19 mole) is added and the reaction mass maintained at 75° C. for 18 hours. Sodium carbonate is then added to adjust the pH to 2–3. Allyl bromide (5.2 g; 0.04 mole) is then added and the reaction mass stirred for a further 2 hours at 75° C. Analysis by GLC indicated an 80% conversion (by area %) to 3-N,N-diallylaminophenol.

We claim:

1. A method of producing N,N-disubstituted aminophenols of the general formula

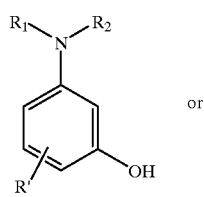
(I)

or

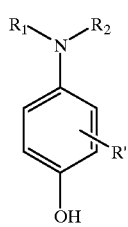
(II)

wherein $R_1$ and $R_2$ are the same or different and each represents a saturated or unsaturated aliphatic hydrocarbyl, cycloalkyl, aralkyl, the phenyl ring of which may be further substituted, alkoxyalkyl, or a cycloalkylalkyl, except that $R_1$ and $R_2$ are not simultaneously methyl and R' represents hydrogen, halogen, nitro, cyano, alkyl or alkoxy, which comprises reacting an aminophenol of general formula

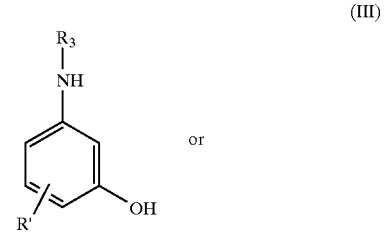
(III)

or

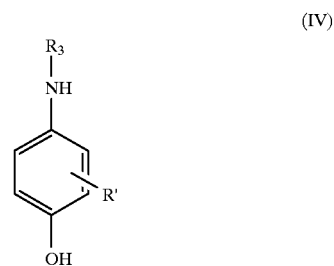
(IV)

wherein $R_3$ represents hydrogen or $R_1$, and R' is as defined above, with an organic halide species of general formula $R_2X$ wherein $R_2$ is as defined above and X is halogen under aqueous acidic conditions with the periodic addition of an acid trapping agent in such a way that continuous monitoring of pH is not required.

2. A method as claimed in claim 1 in which $R_1$ or $R_2$ is a linear or branched alkyl of 1 to 18 carbon atoms; alkenyl having 3 to 5 carbon atoms; alkynyl having 3 carbon atoms; cycloalkyl of 5 to 7 carbon atoms in which the cycloalkyl ring may be further substituted by methyl; aralkyl of 7 to 8 carbon atoms in which the aryl ring may be further substituted; alkoxy of 2 to 4 carbon atoms; cycloalkylalkyl of 6 to 8 carbon atoms in which the cycloalkyl ring may be further substituted by methyl.

3. A method as claimed in claim 1 in which X is chlorine, bromine or iodine.

4. A method as claimed in claim 1 in which R' is hydrogen, chlorine, bromine, nitro, cyano, alkyl of 1 to 2 carbon atoms or alkoxy of 1 to 2 carbon atoms.

5. A method as claimed in claim 1 in which the acid trapping agent is a metal hydroxide or carbonate from Group 1 or 2 of the Periodic Table, or a metal bicarbonate from Group 1 of the Periodic Table.

6. A method as claimed in claim 5 in which the acid trapping agent is lithium hydroxide, sodium hydroxide, potassium hydroxide, magnesium hydroxide, calcium hydroxide, lithium carbonate, sodium carbonate, potassium carbonate, calcium carbonate, magnesium carbonate, sodium bicarbonate or potassium bicarbonate.

7. A method as claimed in claim 5 in which the acid trapping agent is used as a solid, aqueous solution or aqueous slurry.

8. A method as claimed in claim 1 in which the acid trapping agent is magnesium oxide.

9. A method as claimed in claim 1 in which $R_3$ is hydrogen and the organic halide species is used in an amount of 2.0 to 2.5 moles, per mole of starting aminophenol.

10. A method as claimed in claim 1 in which $R_3$ is other than hydrogen and the organic halide species is used in an amount of 1.0 to 1.25 moles per mole of starting aminophenol.

11. A method as claimed in claim 1 in which the water is present in an amount to dissolve, either wholly or in part, the generated halide salts.

12. A method as claimed in claim 1 which is carried out within the temperature range of room temperature to the boiling point of the reaction mass.

13. A method as claimed in claim 12 which is carried out at a temperature of from 50° C. to the boiling point of the reaction mass.

14. A method as claimed in claim 1 in which, after the reaction is complete a water immiscible solvent is added to aid the isolation.

15. A method as claimed in claim 14 in which the solvent is an aromatic hydrocarbon, a chlorinated aromatic hydrocarbon, a saturated or unsaturated aliphatic hydrocarbon optionally substituted by chlorine, or a cycloalkyl compound of 5 to 7 carbon atoms.

16. A method as claimed in claim 1 in which the organic halide species is added in a stepwise manner.

* * * * *